US007648955B2

(12) United States Patent
Dubois et al.

(10) Patent No.: US 7,648,955 B2
(45) Date of Patent: Jan. 19, 2010

(54) FRAGRANCES COMPRISING RESIDUAL ACCORDS

(75) Inventors: Zerlina Guzdar Dubois, Mason, OH (US); Lynette Anne Makins Holland, Watford (GB)

(73) Assignee: The Procter & Gamble Company, Cincinnati, OH (US)

( * ) Notice: Subject to any disclaimer, the term of this patent is extended or adjusted under 35 U.S.C. 154(b) by 637 days.

(21) Appl. No.: 10/981,018

(22) Filed: Nov. 4, 2004

(65) Prior Publication Data

US 2005/0096252 A1 May 5, 2005

Related U.S. Application Data

(60) Provisional application No. 60/517,097, filed on Nov. 4, 2003.

(51) Int. Cl.

*A61K 8/30* (2006.01)
*A61K 8/34* (2006.01)
*A61K 8/35* (2006.01)
*A61Q 1/00* (2006.01)
*A61Q 5/00* (2006.01)
*A61Q 13/00* (2006.01)
*A61Q 15/00* (2006.01)
*A61Q 17/00* (2006.01)
*A61Q 19/00* (2006.01)

(52) U.S. Cl. .................. 512/14; 512/1; 512/8; 512/11; 512/15; 512/16; 512/17; 512/18; 424/70.1; 424/59; 424/65; 424/76.1

(58) Field of Classification Search .................... 512/14
See application file for complete search history.

(56) References Cited

U.S. PATENT DOCUMENTS

| | | | | |
|---|---|---|---|---|
| 5,520,839 | A | 5/1996 | Hall et al. | |
| 5,780,404 | A | 7/1998 | Bacon et al. | |
| 5,833,999 | A | 11/1998 | Trinh et al. | |
| 5,861,146 | A * | 1/1999 | Peterson et al. | 424/65 |
| 5,874,070 | A * | 2/1999 | Trinh et al. | 424/65 |
| 5,942,217 | A | 8/1999 | Woo et al. | |
| 6,129,941 | A * | 10/2000 | Escher et al. | 426/535 |
| 6,204,229 | B1 | 3/2001 | Hasegawa et al. | |
| 6,255,276 | B1 * | 7/2001 | Frater et al. | 512/11 |
| 6,379,681 | B1 | 4/2002 | Bordat et al. | |
| 7,169,746 | B2 * | 1/2007 | Shoji et al. | 512/1 |
| 7,208,462 | B2 * | 4/2007 | Heltovics et al. | 512/1 |
| 2002/0055452 | A1 | 5/2002 | McGee et al. | |
| 2003/0087776 | A1 | 5/2003 | Heltovics et al. | |
| 2003/0134759 | A1 | 7/2003 | Geary et al. | |
| 2003/0136937 | A1 * | 7/2003 | Egawa et al. | 252/8.61 |
| 2003/0166497 | A1 | 9/2003 | Yang et al. | |
| 2003/0166498 | A1 | 9/2003 | Yang et al. | |
| 2003/0166499 | A1 | 9/2003 | Yang et al. | |
| 2004/0091628 | A1 * | 5/2004 | Heltovics et al. | 427/402 |
| 2004/0220064 | A1 * | 11/2004 | McGee et al. | 510/130 |
| 2006/0281648 | A1 * | 12/2006 | Eh | 510/101 |

FOREIGN PATENT DOCUMENTS

| | | | |
|---|---|---|---|
| EP | 0 554 024 | B1 | 7/1997 |
| WO | WO 97/48374 | A2 | 12/1997 |
| WO | WO 97/48375 | A2 | 12/1997 |
| WO | WO 97/48378 | A1 | 12/1997 |
| WO | WO 02/34225 | A1 | 5/2002 |
| WO | WO02/053151 | * | 7/2002 |
| WO | WO 02/098966 | A1 | 12/2002 |
| WO | WO 03/015736 | A2 | 2/2003 |

OTHER PUBLICATIONS

Ansari, S.H., et al., "Essential Oils from Bolivia. I.Asteraceae: *Baccharis tricuneata* (L.f.) Pers. Var. *Ruiziana Cuatrecassas*", Journal of Essential Oil Research, vol. 16, No. 5, pp. 417-419 (Sep./Oct. 2004) (ISSN:1041-2905).
Arze, J.B.L, et al., "Essential Oils from Bolivia. I.Asteraceae: *Baccharis Tricuneata* (L.f.) Pers. Var. *Ruiziana Cuatrecassas*", Journal of Essential Oil Research, vol. 16, No. 5, pp. 429-431 (Sep./Oct. 2004) ISSN:1041-2905).
Kirbalsar, G., et al., "Composition of Turkish Bitter Orange and Lemon Leaf Oils", Journal of Essential Oil Research, vol. 16, No. 2, pp. 105-108 (Mar./Apr. 2004), (ISSN: 1041-2905).
Lawrence, Dr. B. M., "Progress in Essential Oils", Perfume and Flavourist, vol. 24, No. 1, pp. 53-63 (Jan./Feb. 1999), (ISSN: 1041-2905).
Miguel, M.G, et al., "Variation in the Main Components of the Essential Oils from the Leaves and Flowers of Portuguese *Thyumus albicans* Over a Single Seasosn", Journal of Essential Oil Research, vol. 16, No. 3, pp. 169-171 (May/Jun. 2004) (ISSN:1041-2905).
Salido, S., et al. "Chemical Composition and Seasonal Variations of Spike Lavender Oil from Southern Spain", Journal of Essential Oil Research vol. 16, No. 3, pp. 206-210 (May/Jun. 2004). (ISSN: 1041-2905).
Stubbs, B.J., et al., "The Essential Oil of *Cinnamomum camphora* (L.) Nees and Eberm.—Variation in Oil Composition Throughout the Tree in Two Chemotypes from Eastern Australia", Journal of Essential Oil Research, vol. 16, No. 3, pp. 200-205 (May/Jun. 2004) (ISSN: 1041-2905).

* cited by examiner

*Primary Examiner*—Joseph D Anthony
(74) *Attorney, Agent, or Firm*—Mark A. Charles; Cynthis L. Clay

(57) ABSTRACT

A fragrance composition is provided comprising from about 10% wt to about 40% wt of a residual accord, the residual accord comprising perfume raw materials (PRMs) selected from at least three of the five defined classes. In addition, personal care compositions comprising the defined fragrance composition are also provided.

18 Claims, No Drawings

FRAGRANCES COMPRISING RESIDUAL ACCORDS

CROSS REFERENCE TO RELATED APPLICATION

This application claims the benefit of U.S. Application No. 60/517,097, filed Nov. 4, 2003.

FIELD OF THE INVENTION

The present application relates to the field of fragrances, particularly fragrances having a long-lasting character. It also relates to cosmetic compositions comprising such fragrances, especially rinse-off products, such as body washes and shampoos.

BACKGROUND OF THE INVENTION

Fragrances are generally known, as is the addition of fragrances to products, such as cosmetic products, to improve their odour. The addition of such fragrances can be carried out to mask unpleasant odours in the product, to lend a pleasant odour to the substrate (e.g. the human skin) or merely to improve the overall consumer acceptance of the products in question.

Fragrance oils used within cosmetic compositions usually comprise a multitude of different perfume raw materials (PRMs). Perfume raw materials include many odiferous chemical compounds. A wide variety of chemicals is known for fragrance uses, including, without limitation, certain aldehydes, ketones, alcohols, terpenes, amines, ethers, hydrocarbons, imines, lactones, thiols and esters. Certain naturally occurring plant and animal oils comprising complex mixtures of various chemical components may also be used as fragrances. The individual PRMs which make up a natural oil may be found by reference to journals commonly used by those skilled in the art such as "Perfume and Flavourist" (ISSN: 1041-2905) or "Journal of Essential Oil Research" (ISSN: 0272-2666), which references are incorporated herein by reference in their entirety.

Every PRM differs from other PRMs by several important properties, including individual character and the olfactory detection level, known as the odour detection threshold (ODT). ODT is defined for a given material as the lowest vapour concentration of that material which can be olfactorily detected. The odour detection threshold per se and some odour detection threshold values are discussed in eg "Standardized Human Olfactory Thresholds", M. Devos et al, IRL Press at Oxford University Press, 1990, and "Compilation of Odor and Taste Threshold Values Data", F. A. Fazzalar, editor ASTM Data Series DS 48A, American Society for Testing and Materials, 1978. Both of these publications are incorporated by reference.

By bearing in mind properties, such as ODT, PRMs can be blended to develop a fragrance oil with an overall specific character profile. It is usual for the character to be designed to alter and develop over the product use cycle and during the time that the fragrance is deposited on a substrate as the different PRMs evaporate and are detected by the user. For example, PRMs which have a high volatility and low substantivity are commonly used to give an initial impression of characters such as light, fresh, fruity, citrus, green or delicate floral to the fragrance oil—these characters are detected during or soon after application. Such materials are commonly referred to in the field of fragrances as "top notes". In contrast, the less volatile, and more substantive PRMs are typically used to give characters such as musk, sweet, balsamic, spicy, woody or heavy floral to the fragrance oil which, although detectable soon after application, also last for longer. These materials are commonly referred to as "middle notes" or "base notes". Skilled perfumers are usually employed to carefully blend PRMs so that the resultant fragrance oils have the desired overall fragrance character profile.

The physical characteristics of the PRMs themselves may limit the overall fragrance character profiles that can be created by perfumers. One limitation is that the characters remaining on a substrate after several hours, particularly from a rinse off product such as a body wash or a shampoo, are typically dominated by musky characters. The prevalence of these residual characters is so great that modern consumers barely notice them any longer and have little interest in them. They perceive these characters as being the odour that the product itself imparts rather than that of the fragrance. It is therefore desirable to deliver fragrances to a substrate whose residual character, particularly after rinsing or washing, is recognizably different from current musky characters.

The PRMs used in the present invention are known, but they are currently used at only low levels and only in combinations of a few PRMs at a time in any given perfume composition. This is because of the low ODTs exhibitted by these PRMs. It has been generally accepted that combining large numbers of PRMs having low ODTs results in the creation of perfumes which are, at the very least, not aesthetically pleasing and unrounded, and which, at most, can be overpowering and quite unpleasant.

WO 02/34225, teaches compositions comprising enduring fragrances, wherein the enduring nature is achieved by means of fragrance encapsulation in materials such as cyclodextrins. These materials are capable of entraping volatile fragrance oils and then releasing them in response to changes in external conditions, such as exposed to moisture. The presence of such encapsulation materials can be disadvantageous, however, in that they may react with other compositional elements and break down. They may also interfere with the lathering ability of rinse-off personal cleansing compositions.

SUMMARY OF THE INVENTION

Contrary to expectation, the present inventors have established that, by careful selection of PRMs having a low ODT, even at relatively high levels, it is possible to create fragrances that are both residual and pleasant and whose residual character is substantially different from the musky characters which predominate in the marketplace today.

According to a first aspect of the invention, a fragrance composition is provided comprising from about 10% wt to about 40% wt of a residual accord, the residual accord comprising perfume raw materials (PRMs) selected from at least three of the five classes, A-E:

| Class A |
|---|
| Dodecahydro-3a,6,6,9a-tetramethylnaphtho[2,1-b]furan |
| Dodecahydrotetramethylnaphthofuran |
| 1-(2,2,6-trimethylcyclohexyl)-3-hexanol |
| Oxacycloheptadec-10-en-2-one |
| Trimethyl-bicyclo-heptane-spiro-cyclohexenone |
| 4-(2,6,6-trimethyl-1-cyclohexen-1-yl)-3-buten-2-one |
| 8H-Indenol(4,5-B)Furan,Decahydro-2-6,6,7,8,8-hexamethyl |
| 4-(2,6,6-trimethyl-1-cyclohexen-2-yl)-3-buten-2-one |
| 5-(2,6,6-trimethyl-1-cyclohexen-1-yl)-4-penten-3-one |

-continued

| Class A |
| --- |
| Octahydro-2,3,8,8-tetramethyl-2-acetonaphthone |
| Methyl 2,4-dihydroxy-3,6-dimethylbenzoate |

| Class B |
| --- |
| 4-Penten-2-ol, 3,3-dimethyl-5-(2,2,3-trimethyl-3-cyclopenten-1-yl)- |
| 4-Penten-2-ol, 3-methyl-5-(2,2,3-trimethyl-3-cyclopenten-1-yl)- |
| 2-ethyl-4-(2,2,3-trimethylcyclopent-3-enyl-1)-2-buten-1-ol |

| Class C |
| --- |
| 1-(2,6,6-trimethyl-3-cyclohexen-1-yl)-2-buten-1-one |
| 4-(2,6,6-trimethyl-2-cyclohexenyl)-2-butene-4-one |
| 4-(2,6,6-trimethylcyclohex-1-enyl)but-2-en-4-one |
| 3-methoxy-4-hydroxybenzaldehyde |
| 3-ethoxy-4-hydroxybenzaldehyde |
| Decanolide-1,4 |
| Decanolide-1,5 |
| 4-n-amyl-4-hydroxybutyric acid lactone |
| Dodecanolide-1,4 |
| Dodecanolide-1,5 |
| 4-n-heptyl-4-hydroxybutanoic acid lactone |
| 5-n-hexyl-5-hydroxypentanoic acid lactone |
| 4-(2,6,6-trimethylcyclohexa-1,3-dienyl)but-2-en-4-one |
| 4-cyclopentadecen-1-one, (Z)- |
| 2H-Pyran-2-one, tetrahydro-6-(3-pentenyl)- |
| 2(3H)-Furanone, 5-(3-hexenyl)dihydro-5-methyl-, (Z)- |
| 5-methyl-5-Hexyl-Tetrahydrofuran-2-one |

| Class D |
| --- |
| 2-Butanone, 4-(4-hydroxyphenyl)- |
| Oxiranecarboxylic acid, 3-methyl-3-phenyl-, ethyl ester |

| Class E |
| --- |
| 2-ethyl-3-hydroxy(4H)pyran-4-one |
| 1,3-Benzodioxole-5-carboxaldehyde |

According to a second aspect of the invention, cosmetic compositions are provided comprising from 0.1% wt to 30% wt of a fragrance composition according to the first aspect of the invention.

These and other features, aspects, and advantages of the present invention will become evident to those skilled in the art from a reading of the present disclosure.

DETAILED DESCRIPTION OF THE INVENTION

While the specification concludes with claims which particularly point out and distinctly claim the invention, it is believed the present invention will be better understood from the following description.

All weights, measurements and concentrations herein are measured at 25° C. on the composition in its entirety, unless otherwise specified.

Unless otherwise indicated, all percentages of compositions referred to herein are weight percentages of the total composition (i.e. the sum of all components present) and all ratios are weight ratios.

Unless otherwise indicated, any polymer molecular weights are weight average molecular weights.

Unless otherwise indicated, the content of all literature sources referred to within this text are incorporated herein in full by reference.

Except where specific examples of actual measured values are presented, numerical values referred to herein should be considered to be qualified by the word "about".

As discussed above, the residual accord comprises perfume raw materials (PRMs) selected from at least 3 of the 5 classes listed below. For completeness, the following tables also include proprietary names of these materials as well as, in many cases, the Chemical Abstracts Service (CAS) number, which is a well known, generally accessible additional unique identifier of these materials.

Class A

| Chemical name | CAS # | Supplier trade names | Supplier |
| --- | --- | --- | --- |
| Dodecahydro-3a,6,6,9a-tetramethylnaphtho[2,1-b]furan | 6790-58-5 | Ambrox | Firmenich |
| | | Ambrofix | Givaudan |
| | | Ambroxan | Henkel |
| | | Cetalox | Firmenich |
| | | Sylvamber | BASF |
| Dodecahydrotetramethylnaphthofuran | 378-00-9 | Synambran | Fragrance Resources |
| | | Amberlyn | Quest |
| 1-(2,2,6-trimethylcyclohexyl)-3-hexanol | 70788-30-6 | Norlimbanol | Firmenich |
| | | Timberol | Symrise |
| Oxacycloheptadec-10-en-2-one | 28645-51-4 | Ambrettolide | IFF |
| Trimethyl-bicyclo-heptane-spiro-cyclohexenone | 0133636-82-5 | Wolfwood | Firmenich |
| 8H-Indenol(4,5-B)Furan, Decahydro-2-6,6,7,8,8-hexamethyl | N/A | Trisamber | IFF |
| 4-(2,6,6-trimethyl-1-cyclohexen-1-yl)-3-buten-2-one | 14901-07-6 | Ionone beta | various |

-continued

Class A

| Chemical name | CAS # | Supplier trade names | Supplier |
|---|---|---|---|
| 4-(2,6,6-trimethyl-1-cyclohexen-2-yl)-3-buten-2-one | 127-41-3 | Alpha ionone | various |
| 5-(2,6,6-trimethyl-1-cyclohexen-1-yl)-4-penten-3-one | 14901-07-6 | Methyl beta ionone | various |
| Octahydro-2,3,8,8-tetramethyl-2-acetonaphthone | 54464-57-2 | Iso E super | IFF |
| | | Iso Gamma super | IFF |
| | | Boisvelone | BBA |
| | | Iso Velvetone | IFF |
| | | Isocyclemone E | IFF |
| Methyl 2,4-dihydroxy-3,6-dimethylbenzoate | 4707-47-5 | LRG 201 | Givaudan |
| | | Evernyl | Givaudan |
| | | Veramoss | IFF |

Class B

| Chemical name | CAS # | Supplier trade names | Supplier |
|---|---|---|---|
| 4-Penten-2-ol, 3,3-dimethyl-5-(2,2,3-trimethyl-3-cyclopenten-1-yl)- | 107898-54-4 | Polysantol | Firmenich |
| | | Nirvanol | Firmenich |
| 4-Penten-2-ol, 3-methyl-5-(2,2,3-trimethyl-3-cyclopenten-1-yl)- | 67801-20-1 | Ebanol | Givaudan |
| 2-ethyl-4-(2,2,3-trimethylcyclopent-3-enyl-1)- | 28219-61-6 | Dartanol | Firmenich |
| | | Anadol | BBA |
| 2-buten-1-ol | | Bacdanol | IFF |
| | | Sandranol | Symrise |
| | | Sandolen | Symrise |
| | | Bangalol | Quest |
| | | Sanjinol | IFF |

Class C

| Chemical name | CAS # | Supplier trade names | Supplier |
|---|---|---|---|
| 1-(2,6,6-trimethyl-3-cyclohexen-1-yl)-2-buten-1-one | 57378-68-4 | Delta damascone | Various |
| 4-(2,6,6-trimethyl-2-cyclohexenyl)-2-butene-4-one | 43052-87-5 | Alpha damascone | Various |
| 4-(2,6,6-trimethylcyclohex-1-enyl)but-2-en-4-one | 23726-92-3 | Beta damascone | Various |
| 3-methoxy-4-hydroxybenzaldehyde | 121-33-5 | Vanillin | Various |
| 3-ethoxy-4-hydroxybenzaldehyde | 121-32-4 | Ethyl vanillin | Various |
| Decanolide-1,4 | 706-14-9 | Gamma decalactone | Various |
| Decanolide-1,5 | 705-86-2 | Delta decalactone | Various |
| 4-n-amyl-4-hydroxybutyric acid lactone | 104-61-0 | Gamma nonalactone | Various |
| | | Aldehyde C-18 | Fragrance Resources |
| Dodecanolide-1,4 | 2305-05-7 | Gamma dodecalactone | Various |
| Dodecanolide-1,5 | 713-95-1 | Delta dodecalactone | Various |
| 4-n-heptyl-4-hydroxybutanoic acid lactone | 104-67-6 | Gamma undecalactone | Various |
| | | Aldehyde C-14 | Fragrance Resources |
| | | Peach aldehyde | IFF |
| 5-n-hexyl-5-hydroxypentanoic acid lactone | 211-915-1 | Delta undecalactone | Various |
| 4-(2,6,6-trimethylcyclohexa-1,3-dienyl)but-2-en-4-one | 23696-85-7 | Damascenone | Various |

-continued

| Class C | | | |
|---|---|---|---|
| Chemical name | CAS # | Supplier trade names | Supplier |
| 4-cyclopentadecen-1-one, (Z)- | 0014595-54-1 | Exaltenone | Firmenich |
| 2H-Pyran-2-one, tetrahydro-6-(3-pentenyl)- | 32764-98-0 | Jasmolactone | Firmenich |
| 2(3H)-Furanone, 5-(3-hexenyl)dihydro-5-methyl-, (Z)- | 488-10-8 | Cis jasmone | Various |
| 5-methyl-5-Hexyl-Tetrahydrofuran-2-one | 7011-83-8 | Lactojamon<br>gamma methyl decalactone | Symrise<br>various |

| Class D | | | |
|---|---|---|---|
| Chemical name | CAS # | Supplier trade names | Supplier |
| 2-Butanone, 4-(4-hydroxyphenyl)- | 5471-51-2 | Para hydroxy phenyl butanone<br>Oxanone<br>Oxyphenylon<br>Frambinon<br>Raspberry ketone | Fragrance Resources<br>Symrise<br>IFF<br>Symrise<br>various |
| Oxiranecarboxylic acid, 3-methyl-3-phenyl-, ethyl ester | 77-83-8 | Ethyl methylphenylglycidate<br>Aldehyde C-16<br>Strawberry Pure | various<br>Fragrance Resources<br>Givaudan |

| Class E | | | |
|---|---|---|---|
| Chemical name | CAS # | Supplier trade names | Supplier |
| 2-ethyl-3-hydroxy(4H)pyran-4-one | 4940-11-8 | Ethyl maltol | Various |
| 1,3-Benzodioxole-5-carboxaldehyde | 120-57-0 | Heliotropin | Various |

The fragrance composition according to the invention comprises from about 10% wt to about 40% wt of the residual accord, preferably from about 10% wt to about 30% wt, more preferably from about 15% wt to about 30% wt, more preferably still from about 15% wt to about 25% wt.

Advantageously, the residual accord comprises PRMs selected from at least one of classes A, B or C.

If one of the five classes from which PRMs are selected is Class A, then it is preferred that at least three PRMs be selected from that class.

If one of the five classes from which PRMs are selected is Class C, then it is preferred that at least six PRMs be selected from that class.

Advantageously, the residual accord comprises PRMs selected from four of the five classes, A-E.

Importantly, neither the residual accords, nor the fragrance compositions themselves according to the invention need to be encapsulated in any other material, such as starch or cyclodextrin, as has been carried out by other workers in the past. Indeed, it is preferred that neither the residual accords, nor the fragrance compositions according to the invention be encapsulated, because the presence of such additional materials may cause formulational difficulties and, in any case represents an additional and unnecessary cost. The fragrance compositions according to the invention are designed to have a residual character without the need for additional encapsulation materials.

The balance of the fragrance composition may be made up of complementary PRMs, PRM-solubilisers or mixtures of these materials.

Complementary PRMs according to the invention may comprise any PRMs known to a person skilled, provided that they do not belong to Classes A-E listed hereinabove. Non-limiting examples of such complementary PRMs include adoxal, allyl amyl glycolate, allyl cyclohexane propionate, alpha pinene, alpha terpineol, amyl cinnamic aldehyde, amyl salicylate, anethol, anisic aldehyde, benzaldehyde, benzyl acetate, benzyl acetone, benzyl alcohol, benzyl benzoate, benzyl salicylate, bergamot, beta gamma hexenol, beta naphthol methyl ether, beta pinene, borneol, bornyl acetate, bourgeonal, butyl anthranilate, calone, camphor, carvacrol, carvone, cashmeran, cis-3-hexenyl acetate, cis-3-hexenyl benzoate, cis-3-hexenyl salicylate, cis 1,3-oxathiane-2-methyl-4-propyl acetate, citral, citronellal nitrile, citronellol, citronellyl acetate, coronol, coumarin, 8-cyclohexadecen-1-one, cyclogalbanate, cyclal C, cyclemax, cymal, decyl alcohol, decyl aldehyde, delta muscenone, dihydro iso jasmonate, dihydro myrcenol, dimethyl benzyl carbinol, dimetol, dimethyl benzyl carbinyl butyrate, dimethyl benzyl carbinyl isobutyrate, ethyl aceto acetate, ethyl butyrate, ethyl caproate, ethylene brassylate, ethyl-2-methyl butyrate, ethyl linalool, eucalyptol, eugenol, flor acetate, florol, florosa, exaltolide/cyclopentadecanolide, floralozone, florhydral, frutene, fructone, galaxolide, geraniol, geranyl acetate, geranyl nitrile, habanolide, helional, herbavert, hexyl acetate, hexyl cinnamic aldehyde, hexyl salicylate, hivernal, hydroquinone dimethyl ether, hydroxycitronellal, indol, indolene, intreleven aldehyde, ionone gamma methyl, iso-amyl acetate, iso-amyl alcoho, iso cyclo citral, iso eugenol, iso eugenol acetate, iso propyl quinoline, lilial, limonene, linalool, linalool oxide, linalyl acetate, lyral, mandarinal, menthol, melonal, 2-methoxy-3-(2-methylpropyl)-pyrazine, methyl anthranilate, methyl beta naphthyl ketone, methyl cedrylone, methyl dihydro jasmonate, methyl heptine carbonate, methyl isobutenyl tetrahydro pyran, methyl octine carbonate, methyl phenyl carbinyl acetate, myrecene, neobutenone, neofolione, nerol, 2,6-nonenol, phenoxy ethyl isobutyrate, phenyl acetaldehyde dimethyl acetal, phenyl carbinyl acetate, phenyl ethyl alcohol, phenyl ethyl dimethyl carbino, phenyl propyl alcohol, prenyl acetate, 2,6-nonadienal, 2,6-nonadien-1-ol, nonyl aldehyde, octyl aldehyde, para cymene, para cresol, pentalide, phenyl acetaldehyde, phenoxanol, phenoxy ethyl propionate, sandalore, sandela, tetrahydrolinalool, thymol, tridecene-2-nitrile, trifone, triethyl citrate, triplal, tuberosa, undecavertol, undecylenic aldehyde, undecyl aldehyde, veloutone, verdox, vemaldehyde, zingerone and mixtures thereof.

PRM-solubilisers according to the invention include dipropylene glycol, propylene glycol, isopropyl myristate, diethyl phthalate and mixtures thereof. Fragrance compositions according to the invention may comprise from about 0 to about 90% wt, preferably from about 0.01 to about 40% wt, more preferably from about 0.1 to about 20% wt, more preferably still about 0.5% wt to about 15% wt.

A broad range of suitable perfume raw materials can be found in U.S. Pat. Nos. 4,145,184, 4,209,417, 4,515,705, and 4,152,272, which are incorporated herein by reference.

According to a second aspect of the invention, cosmetic compositions are provided comprising from 0.1% wt to 30% wt of a fragrance composition according to the first aspect of the invention. The term "cosmetic compositions" includes, without limitation, rinse off compositions, such as a bar soaps, liquid soaps, body washes, conditioners and shampoos; leave-on products, such as skin creams, for example facial and body creams and lotions and fine fragrance products. Preferably, the cosmetic composition is a rinse off composition, such as a bar soap, liquid soap, a body wash, conditioner or a shampoo, in which case it advantageously comprises from 0.1% wt to 15% wt of a fragrance composition according to the first aspect of the invention. More preferably, the cosmetic composition is a body wash or a shampoo, in which case it advantageously comprises from 0.1% wt to 10% wt of a fragrance composition according to the first aspect of the invention.

Cosmetic compositions may additionally comprise other elements such as, without limitation, surfactants, emollients, thickeners, moisturisers, preservatives, alcohols and dyes.

The following examples further describe and demonstrate the preferred embodiments within the scope of the present invention. The examples are given solely for the purpose of illustration, and are not to be construed as limitations of the present invention since many variations thereof are possible without departing from its scope.

EXAMPLES

Residual Accord Examples

Residual accord 1

| Perfume material | Class | Level wt % |
|---|---|---|
| Ambrofix | A | 3.355 |
| Ionone Beta | A | 13.434 |
| Iso E Super | A | 46.974 |
| Lrg 201 | A | 0.662 |
| Polysantol | B | 5.033 |
| Sanjinol | B | 20.132 |
| Beta damascone | C | 0.006 |
| Delta Damascone | C | 1.015 |
| Gamma Decalactone | C | 0.662 |
| Gamma Undecalactone | C | 4.017 |
| Vanillin | C | 0.022 |
| Para Hydroxy Phenyl Butanone | D | 3.364 |
| Heliotropin | E | 1.324 |
| Total | | 100 |

-continued

Residual accord 1

| Perfume material | Class | Level wt % |
|---|---|---|

Residual accord 2

| Perfume Materials | Class | Level wt % |
|---|---|---|
| Ambroxan | A | 3.56 |
| Ionone Beta | A | 14.23 |
| Iso Gamma Super | A | 35.58 |
| Lrg 201 | A | 0.71 |
| Norlimbanol | A | 1.42 |
| Trisamber | A | 7.12 |
| Dartanol | B | 0.71 |
| Bacdanol | B | 7.12 |
| Aldehyde C-18 | C | 3.56 |
| Delta Damascone | C | 1.07 |
| Gamma Decalactone | C | 7.12 |
| Vanillin | C | 7.12 |
| Delta Undecalactone | C | 7.12 |
| Para Hydroxy Phenyl Butanone | D | 3.56 |
| Total | | 100 |

Fragrance Composition Examples

| Perfume material | Supplier | Level wt % |
|---|---|---|
| Fragrance composition 1 | | |
| Residual accord 1 | | 23.08 |
| Coronol | Givaudan | 4.64 |
| Cyclo Galbanate | Symrise | 0.31 |
| Ethyl-2-methyl Butyrate | various | 0.77 |
| Galaxolide | IFF | 15.48 |
| Ionone Gamma Methyl | various | 7.74 |
| Lyral | IFF | 10.83 |
| Mandarinal | Firmenich | 0.15 |
| Methyl Dihydro Jasmonate | various | 24.76 |
| Phenoxanol | IFF | 7.74 |
| Delta Muscenone | Firmenich | 0.15 |
| Undecavertol | Givaudan | 3.87 |
| Benzyl alcohol | various | 0.48 |
| Total | | 100 |
| Fragrance composition 2 | | |
| Residual accord 2 | | 14.05 |
| Coronol | Givaudan | 10.00 |
| Cyclo Galbanate | Symrise | 0.20 |
| Ethyl-2-methyl Butyrate | various | 0.50 |
| Galaxolide | IFF | 10.00 |
| Ionone Gamma Methyl | various | 5.00 |
| Lyral | IFF | 3.00 |
| Mandarinal | Firmenich | 0.10 |
| Methyl Dihydro Jasmonate | various | 20.00 |
| Phenoxanol | IFF | 5.00 |
| Undecavertol | Givaudan | 2.50 |
| Hexyl Cinnamic Aldehyde | Various | 10.00 |
| Florosa | Quest | 10.00 |
| Linalool | various | 9.65 |
| Total | | 100 |

Personal Care Composition Examples

| INGREDIENT CHEMICAL/INCI NAME | Bodywash A | Bodywash B | Shampoo C |
|---|---|---|---|
| Water | qs | qs | qs |
| Sodium Laureth 3 Sulphate | | 5.5000 | |
| Sodium Laureth 2 Sulphate | 8.0000 | | |
| Sodium Lauryl Sulfate | 3.0000 | | |
| Ammonium Lauryl Sulfate | | | 8.0000 |
| Ammonium Laureth 3 Sulfate | | | 12.0000 |
| Cocamidopropyl Betaine | 3.0000 | 5.0000 | |
| Sodium Lauroyl Sarcosinate | 3.0000 | 0.5000 | |
| Cocamido MEA | | | 1.0000 |
| Trihydroxystearin | 0.5000 | | |
| Polyquaternium - 10[1] | | 0.1000 | |
| Polyquaternium - 10[2] | 0.2000 | | |
| Polyquaternium - 10[3] | | | 0.5000 |
| PEG 7M | | | 0.1000 |
| Citric Acid | Max 1 | Max 1 | Max 1 |
| Sodium Hydroxide | Max 0.3 | Max 0.3 | Max 0.3 |
| Sodium Sulfate | 4.0000 | 1.5000 | |
| Sodium Chloride | | | 0.2000 |
| Tetrasodium EDTA | 0.1500 | 0.1500 | 0.1300 |
| Sodium Benzoate | 0.2500 | 0.2500 | 0.2500 |
| DMDM Hydantion | 0.2000 | 0.2000 | 0.0500 |
| Lauric Acid | 0.5000 | | 0.5000 |
| Lauryl Alcohol | | 1.0000 | |
| Cetyl Alcohol | | | 1.0000 |
| Fragrance 1 | 4.000 | | 0.8000 |
| Fragrance 2 | | 0.8000 | |
| Hydrogenated Polydecene | | | 0.3000 |
| D&C Red 33 | | 0.0003 | |
| FD&C Green 3 | | 0.0001 | |
| EGDS | 2.0000 | | 1.5000 |

INGREDIENT DETAILS/SUPPLIERS

| INGREDIENT CHEMICAL/INCI NAME | INGREDIENT TRADE NAME | Supplier |
|---|---|---|
| Sodium Lauryl Sulfate | | |
| Cocoamidopropyl Betaine | | Goldschmidt-Degussa |
| Sodium Laureth 3 Sulphate | Empicol ESC70, | Huntsman |
| Sodium Laureth 3 Sulphate | Steol CS330 | Stepan |
| Sodium Laureth 2 Sulphate | Empicol ESB70, | Huntsman |
| Ammonium Lauryl Sulfate | Ammonium Lauryl Sulfate | Manro, Stalybridge, UK |
| Ammonium Laureth 3 Sulfate | Ammonium Laureth 3 Sulfate | Manro, Stalybridge, UK |
| Cocamidopropyl Betaine | Tego Betain-F | Goldschmidt-Degussa |
| Sodium Lauroyl Sarcosinate | Hamposyl L-95, Hamposyl L30 | Dow |
| Cocamide MEA | Monamid CMA | Uniqema, Patterson, NJ |
| Polyquaternium - 10[1] | Polymer JR30M | Amerchol Corp, Edison, N.J USA |
| Polyquaternium - 10[2] | Polymer KG30M | Amerchol Corp, Edison, N.J USA |
| Polyquaternium - 10[3] | Polymer LR400 | Amerchol Corp, Edison, N.J USA |
| Citric Acid | Citric Acid | Roche |
| Sodium Hydroxide | Sodium Hydroxide | |
| Sodium Sulfate | Sodium Sulfate | Ashland/Giles Chemicals |
| Sodium Chloride | Sodium Chloride | Cargill Salt/Breaux Bridge, Louisiana |
| Trihydroxystearin | Thixcin-R | Rheox Inc |

-continued

INGREDIENT DETAILS/SUPPLIERS

| INGREDIENT CHEMICAL/INCI NAME | INGREDIENT TRADE NAME | Supplier |
|---|---|---|
| EGDS | Tegopearl N-100 | Goldschmidt-Degussa |
| Tetrasodium EDTA | Dissolvaine 220 | Akzo Nobel |
| Sodium Benzoate | Sodium Benzoate | Merck GmbH |
| DMDM Hydantion | Glydant 55 | Lonza |
| Lauric Acid | Emery 652 | Cognis |
| PEG 7M | Polyox WSR N-750 | Amerchol Corp, Edison, N.J USA |
| Hydrogenated Polydecene | SynFluid PAO 6cst | Chevron Philips Chemical Co, Texas, USA |
| Cetyl Alcohol | Cetyl Alcohol | Goldschmidt-Degussa |
| D&C Red 33 | D&C Red 34 | Sensient (Warner Jenkinson (LCW), 2526 Baldwin Road, St Louis, Mo. 63105 |
| FD&C Green 3 | FD&C Green 3, WJ#6503 | Sensient (Warner Jenkinson (LCW), 2526 Baldwin Road, St Louis, Mo. 63106 |

It is understood that the examples and embodiments described herein are for illustrative purposes only and that various modifications or changes in light thereof will be suggested to one skilled in the art without departing from the scope of the present invention.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A fragrance composition comprising from about 15% wt to about 40% wt of a residual accord, the residual accord comprising perfume raw materials (PRMs) selected from at least three of the five classes, A-E:

Class A:

Dodecahydro-3a,6,6,9a-te-tramethylnaphtho[2,1-b]furan;

Dodecahydrotetramethylnaphthofuran;

1-(2,2,6-trimethylcyclohexyl)-3-hexanol;

Oxacycloheptadec-10-en-2-one;

Trimethyl-bicyclo-heptane-spiro-cyclohexenone;

4-(2,6,6-trimethyl-1-cyclohexen-1-yl)-3-buten-2-one;

8H-Indenol(4,5-B)Furan,Decahydro-2-6,6,7,8,8-hexamethyl;

4-(2,6,6-trimethyl-1-cyclohexen-2-yl)-3-buten-2-one;

5-(2,6,6-trimethyl-1-cyclohexen-1-yl)-4-penten-3-one;

Octahydro-2,3,8,8-tetramethyl-2-acetonaphthone;

Methyl 2,4-dihydroxy-3,6-dimethylbenzoate;

Class B:

4-Penten-2-ol, 3,3-dimethyl-5-(2,2,3-trimethyl-3-cyclopenten-1-yl);

4-Penten-2-ol, 3-methyl-5-(2,2,3-trimethyl-3-cyclopenten-1-yl);

2-ethyl-4-(2,2,3-trimethylcyclopent-3-enyl- 1)-2-buten-1-ol;

Class C:
1-(2,6,6-trimethyl-3-cyc-lohexen-1-yl)-2-buten-1-one;
4-(2,6,6-trimethyl-2-cyclohexenyl)-2-b-utene-4-one;
4-(2,6,6-trimethylcyclohex-1-enyl)but-2-en-4-one;
3-methoxy-4-hydroxybenzaldehyde;
3-ethoxy-4-hydroxybenzaldehyde;
Decanolide-1,4;
Decanolide-1,5;
4-n-amyl-4-hydroxybutyric acid lactone;
Dodecanolide-1,4;
Dodecanolide-1,5;
4-n-heptyl-4-hydroxybutanoic acid lactone;
5-n-hexyl-5-hydroxypentanoic acid lactone;
4-(2,6,6-trimethylcyclohexa-1,3-dienyl)but-2-en-4-one;
4-cyclopentadecen-1-one, (Z)-;
2H-Pyran-2-one, tetrahydro-6-(3-pentenyl)-;
2(3H)-Furanone, 5-(3-hexenyl)dihydro-5-methyl-, (Z)-;
5-methyl-5-Hexyl-Tetrahydrofuran-2-one;
Class D:
2-Butanone, 4-(4-hydroxyphenyl)-;
Oxiranecarboxylic acid, 3-methyl-3-phenyl-, ethyl ester;
Class E:
2-ethyl-3-hydroxy(4H)pyran-4-one;
1,3-Benzodioxole-5-carboxaldehyde;
wherein the residual accord comprises at least six PRMs selected from Class C.

2. The fragrance composition of claim 1, wherein the residual accord comprises PRMs selected from Class A.

3. The fragrance composition of claim 1, wherein the residual accord comprises at least three PRMs selected from Class A.

4. The fragrance composition of claim 1, wherein the residual accord comprises PRMs selected from Class B.

5. The fragrance composition of claim 1, wherein the residual accord comprises PRMs selected from Classes A and C.

6. The fragrance composition of claim 5, wherein the residual accord comprises at least three PRMs selected from Class A.

7. The fragrance composition of claim 1, wherein the residual accord comprises PRMs selected from at least four of the five classes, A-E.

8. The fragrance composition of claim 7, wherein the residual accord comprises PRMs selected from Classes A and C.

9. The fragrance composition comprising from about 15 to about 30% wt of a residual accord of claim 1.

10. The fragrance composition comprising from about 15 to about 25% wt of a residual accord of claim 1.

11. The fragrance composition of claim 1, additionally comprising a PRM solubiliser.

12. The fragrance composition of claim 11, wherein the PRM-solubiliser is selected from the group consisting of dipropylene glycol, propylene glycol, isopropyl myristate, diethyl phthalate, and mixtures thereof.

13. The fragrance composition of claim 1 which is non-encapsulated.

14. A cosmetic composition comprising from about 0.1 to about 30% of the fragrance composition of claim 1.

15. A cosmetic composition comprising from about 0.1% wt to about 15% wt of the fragrance composition of claim 1.

16. A body wash composition comprising from about 0.1% wt to about 10% wt of the fragrance composition of claim 1.

17. A shampoo composition comprising from about 0.1% wt to about 10% wt of the fragrance composition of claim 1.

18. A fragrance composition comprising from about 10% wt to about 40% wt of a residual accord, the residual accord comprising perfume raw materials (PRMs) comprising Dodecahydro-3a,6,6,9a-tetramethylnaphtho [2,1-b]furan, 2-ethyl-4-(2,2,3-trimethylcyclopent-3-enyl-1)-2-buten-1-ol and 3-methoxy-4-hydroxybenzaldehyde.

* * * * *

UNITED STATES PATENT AND TRADEMARK OFFICE

CERTIFICATE OF CORRECTION

PATENT NO. : 7,648,955 B2
APPLICATION NO. : 10/981018
DATED : January 19, 2010
INVENTOR(S) : Dubois et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1126 days.

Signed and Sealed this

Twenty-eighth Day of December, 2010

David J. Kappos
*Director of the United States Patent and Trademark Office*